United States Patent [19]

McRae

[11] Patent Number: Plant 6,505

[45] Date of Patent: Jan. 3, 1989

[54] HYBRID ORIENTAL LILY NAMED ISADORA

[75] Inventor: Edward A. McRae, Boring, Oreg.

[73] Assignee: Melridge, Inc., Gresham, Oreg.

[21] Appl. No.: 38,763

[22] Filed: Apr. 15, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid Oriental lily plant bearing large, upright to semi-upright flowers particularly characterized by their clear pink coloration on a broad white background, the flowers being of excellent form and long persistence both on the plant and as cut flowers. The very large size and substance of these flowers and their upright to semi-upright orientation is a combination that is completely new in the Oriental hybrid divisions of lilies suited to forcing and to mass commercial cultivation. The plant is highly resistant to disease and shows tolerance of virus, it is an excellent garden plant, and its bulbs may be precooled and forced for cut flower production.

1 Drawing Sheet

BACKGROUND OF THE NEW PLANT

This new lily plant originated as a seedling selected by me from a group of seedlings planted by me at Sandy, Oreg., with the object of producing Oriental hybrids having large flowers, with a generally upright orientation, in the shades of soft pink and white suited to forcing into flower out-of-season, heretofore unknown in the lily breeding art, the seeds for the said planting being from a hybrid resulting from my crossing a selected clone from the strain 'Pink Glory' as the mother plant with a selected form of the species *Lilium nobilissimum* as the pollen parent. To achieve the crossing of these distantly related lilies, I found it necessary to maintain extremely high greenhouse temperatures for at least one week after pollination. The flowers of this selected seedling are characterized by an upright to semi-upright orientation, extremely large size and broad tepalled "bowl-shaped" form with unusually thick substance and a distinctive clear pink coloration extending centrally along each tepal and bordered with broad white margins, this combination being unique among Oriental hybrid lilies, and because of these exceptional characteristics, the selected plant was asexually reproduced by me and under my direction at Sandy, Oregon, with such success that successive generations were produced under my direction at Sandy, Oregon, by natural propagation from bulblets, by bulb scale propagation, and by tissue culturing from bulb scale explants. This work with my new variety has demonstrated that the novel and distinctive characteristics of the new variety are fixed and hold true under asexual propagation from generation to generation.

Our work with this new Oriental lily variety has demonstrated that it possesses unusually strong, stout stems with exceptionally broad leaves, and in addition, the clone possesses to a high degree the desirable characteristics of hybrid vigor, great hardiness and disease resistance, as well as possessing all of the desired characteristics of excellence of form, color and habit; the clone being vigorous and a good grower and propagator, as observed at Sandy, Oreg.

The new plant is well suited to forcing out-of-season when the bulbs are dug at the proper time and properly precooled. For example, late October-dug bulbs properly precooled and potted in January will flower under glass in western Oregon in an average of one hundred to one hundred fifteen days, with no supplementary lighting and at moderate greenhouse temperatures.

DESCRIPTION OF THE DRAWING

My new variety of lily plant is illustrated by the accompanying photographic drawing, which shows the open bloom in full color and illustrates the flower form, the tepal arrangement, and in particular, the novel and distinctive flower size, form and upright to semi-upright orientation, as well as the clear pink coloration extending lengthwise of the tepals between broad white margins, the colors shown being as nearly true to those specified as is reasonably possible to obtain by professional photographic procedures.

DESCRIPTION OF THE NEW VARIETY

The following is a detailed description of my new variety of hybrid Oriental lily with nomenclature according to The International Lily Register of The Royal Horticultural Society of London, England (Second Edition, 1969), and with color designations according to The R.H.S. Colour Chart published in 1966 by The Royal Horticultural Society.

THE PLANT

Origin: Seedling.

Parentage:

*Seed parent.*—A selected clone from the 'Pink Glory' strain (unpatented).

*Pollen parent.*—A selected clone of *Lilium nobilissimum* (unpatented).

Classification:

*Horticultural.*—Division VII-B, Bown-shaped Oriental Lily, according to The Horticultural Classification of Lilies by The Royal Horticultural Society of London.

*Commercial.*—Hybrid Lilium Clone.

Form: Single stem, erect and stately.

Height: About 70 to 125 cm. from bulbs of about 14 to 18 cm. in circumference; provided that their light levels are adequate. Low light levels may cause "stretching".

Growth: Vigorous and upright.

Foliage:

*Quantity.*—Abundant.

*Leaf size.*—Unusually broad, about 7 to 8 cm. wide and about 12 to 15 cm. long.

*Leaf shape.*—Lanceolate with acuminate tip.

*Texture.*—Leathery.

*Aspect.*—Glossy.

*Color.*—Medium green, lighter on the lower side.

Bulbs:

*Size.*—Varying and ranging up to 25 cm. in circumference as commercially used.

*Color.*—White, with flushes of soft pink or soft yellow after exposure to light.

THE BUD

Form: Long ovoid with obtuse base and acute tip.

Size: About 9 to 12 cm. long and about 10 to 12 cm. in circumference just prior to opening.

Opening rate: The bud opens slowly, taking about an hour in response to morning light.

Color: White with a soft flush of pink in the middle of the bud, and soft green midribs.

Peduncle:

Length.—About 4 to 6 cm., in average, but length may increase if light levels are too low or if the bulbs have been improperly stored prior to forcing.

*Color.*—Medium green with very light plum overlay.

THE FLOWER

Blooming habit: Once annually and profusely in midseason.

Size: Large; averaging about 18 to 23 cm. in diameter, reflexing at the tips on the second day to provide a spread of about 15 to 18 cm. in diameter.

Borne: In a single raceme including from three to six flowers, from a bulb about 14 to 16 cm. in circumference.

Shape: Opening to a broad bowl shape by the second day with the bowl being about 10 cm. deep.

Tepalage:

*Number.*—Typical of genus Lilium with six imbricated tepals in hexagonal arrangement.

*Size.*—Outer tepals are about 3 to 3.5 cm. wide and the inner tepals are about 5 to 5.5 cm. wide.

*Color.*—The flowers are distinguished by their clear pink coloration, 66C-D, along the midrib which suffuses laterally from above the nectaries to a lighter pink, 68A-B, near the tepal margins, which are pure white and about 2 to 3 cm. wide, and broadening to about 4 cm. wide adjacent the tepal apex. The nectary furrows are apple green.

*Spotting.*—The flowers have only a few small and inconspicuous spots, there being about five to twenty medium pink spots on each inner tepal adjacent the nectaries.

*Appearance.*—The tepals are shiny.

*Longevity.*—The tepals stay on the stems about three weeks.

Color changes: The flowers become slightly lighter and a more lavender-toned pink, approaching 65B-C to 68D, as the flowers age. Low light levels and extreme heat may cause the pink pigmentation to decrease.

Fragrance: Distinct and pleasing.

Pedicel:

*Length.*—About 8 to 12 cm., in average.

*Form.*—Sturdy and ascending up to about 45 degrees from the horizontal.

*Color.*—Medium green with very light plum overlay.

Disease resistance: The flower and plant are resistant to disease; in particular, they are resistant to Fusarium bulb rot and Botrytis blight.

Lasting quality: The flower is long lasting, both on the plant and as a cut flower.

REPRODUCTIVE ORGANS

Stamens:

*Number.*—Six.

*Arrangement.*—Typical of the genus Lilium.

*Anthers (Dehisced) and pollen.*—Color: Greyed red, 179A.

*Filaments.*—Length: About 8 to 10 cm. Color: Soft green to white.

Pistil:

*Number.*—One.

*Length.*—About 8 to 10 cm.

*Stigma.*—Size: Large. Color: Soft greenish white with a very light pink overlay.

Characteristics of ovary: The ovary is characteristic of the genus Lilium.

THE FRUIT

Fertility: The fruit is fertile.

Shape: Ovoid. p0 Color at maturity: Soft brown, sometimes overlaid with soft plum.

This new variety of hybrid Oriental lily most nearly resembles 'Pink Glory' (unpatented) but it has much larger, thicker, and more bowl-shaped flowers, which, in orientation, are more upright to semi-upright rather than side-facing. The leaves of this new plant are much broader and its stems are stronger and stockier. This plant can be distinguished from its sister clones by the much broader white margins on the tepals of its flowers.

I claim:

1. The new and distinctive variety of hybrid Oriental lily plant and parts thereof, substantially as herein shown and described, characterized by its unique upright to semi-upright flowers having a clear pink coloration extending along each tepal midrib between broad white margins, the excellence of its flower form, size and substance, and its versatility both as a garden plant and as a cut flower producer from precooled bulbs forced under glass out-of-season, its vigorous growth and rapid natural propagation, and its resistance to disease and tolerance of virus.

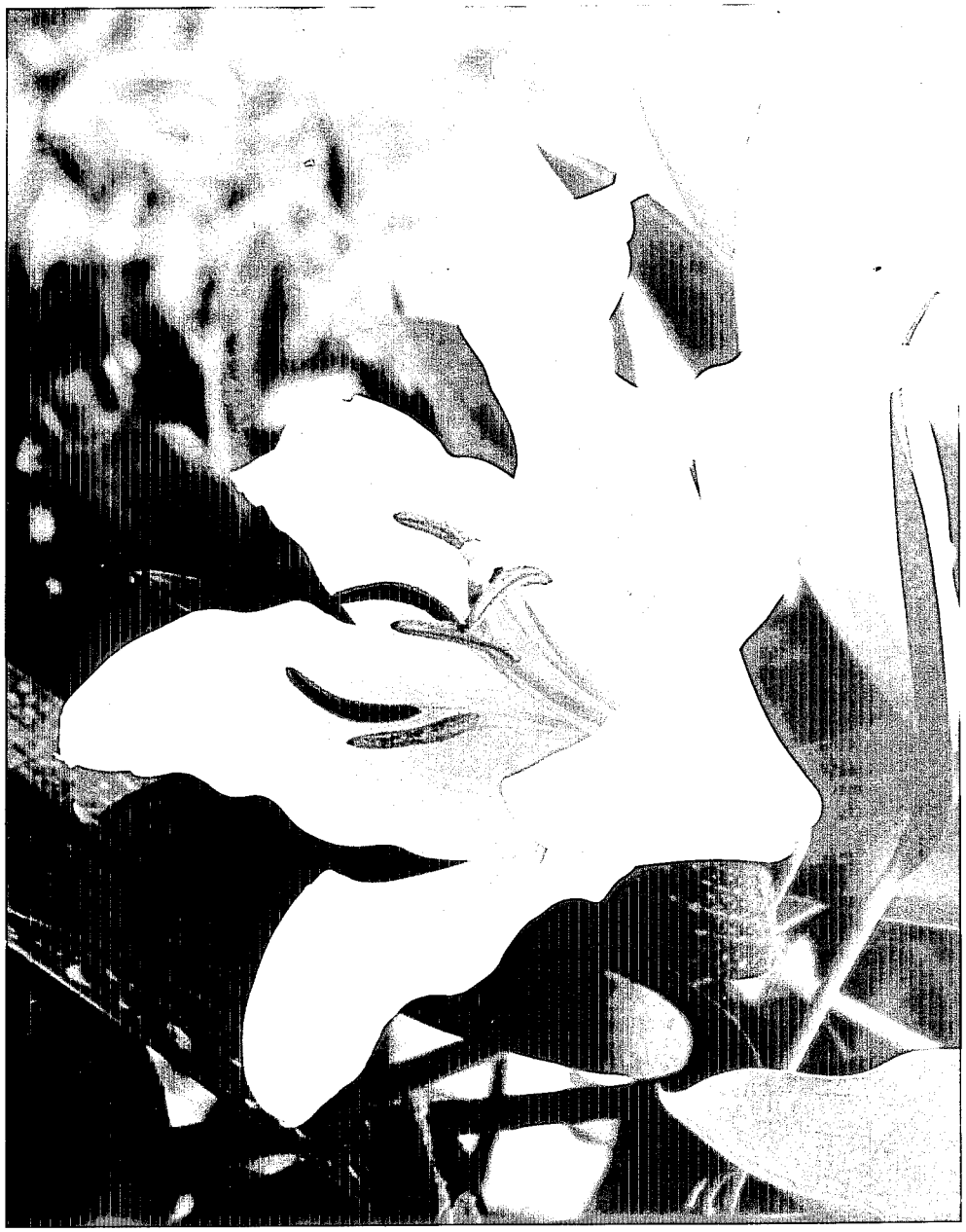

* * * * *